United States Patent
Wong

(10) Patent No.: US 8,729,475 B1
(45) Date of Patent: May 20, 2014

(54) ABSORPTION BIASED SINGLE BEAM NDIR GAS SENSOR

(71) Applicant: Airware, Inc., Goleta, CA (US)

(72) Inventor: Jacob Y Wong, Goleta, CA (US)

(73) Assignee: Airware, Inc., Goleta, CA (US)

( * ) Notice: Subject to any disclaimer, the term of this patent is extended or adjusted under 35 U.S.C. 154(b) by 0 days.

(21) Appl. No.: 14/065,943

(22) Filed: Oct. 29, 2013

Related U.S. Application Data

(60) Provisional application No. 61/891,222, filed on Oct. 15, 2013.

(51) Int. Cl.
*G01N 21/61* (2006.01)

(52) U.S. Cl.
CPC ........ *G01N 21/61* (2013.01); *G01N 2201/0662* (2013.01); *G01N 2201/066* (2013.01)
USPC .......................................................... 250/343

(58) Field of Classification Search
CPC .............. G01N 2021/1759; G01N 2201/0668; G01N 2201/066; G01N 2201/0662; G01N 33/004; G01N 21/61
USPC .......................................................... 250/343
See application file for complete search history.

(56) References Cited

U.S. PATENT DOCUMENTS

| | | | |
|---|---|---|---|
| 6,075,246 A | 6/2000 | Stock | |
| 8,143,581 B2 | 3/2012 | Wong | |
| 8,148,691 B1 | 4/2012 | Wong | |
| 8,178,832 B1 | 5/2012 | Wong | |
| 8,217,355 B1 | 7/2012 | Wong | |
| 8,415,626 B1 | 4/2013 | Wong | |
| 2008/0035848 A1 | 2/2008 | Wong | |
| 2012/0330568 A1* | 12/2012 | Izawa et al. | 702/24 |

FOREIGN PATENT DOCUMENTS

| | | | |
|---|---|---|---|
| JP | 2006153543 A | * | 6/2006 |
| JP | 2012108009 A | * | 6/2012 |

OTHER PUBLICATIONS

JP 2012-1008009 A Machine translation.*
JP 2006-153543 A Machine Translation.*
Jacob Y. Wong; Roy L. Anderson; Non-dispersive Infrared Gas Measurement; IFSA Publishing; 2012; Barcelona, Spain.

* cited by examiner

*Primary Examiner* — Constantine Hannaher
(74) *Attorney, Agent, or Firm* — Roy L. Anderson; Wagner, Anderson + Bright PC

(57) ABSTRACT

An Absorption Biased (AB) methodology for NDIR gas sensors is used with a single infrared source and a detector to detect a single gas of interest by using a motion device to change the path length between that of the signal and reference channels. As in the case of the AB designed NDIR gas sensor, the ratio of the output of the Signal channel, measured during location arrangement X, over that of the Reference channel, measured during location arrangement Y, will be used to process the gas measurement. Multiple gases of interest can be detected by using one detector to detect multiple gases and/or by locating a second detector to detect multiple gases more distant from the source than the first detector, thereby creating longer path lengths for the second detector.

18 Claims, 4 Drawing Sheets

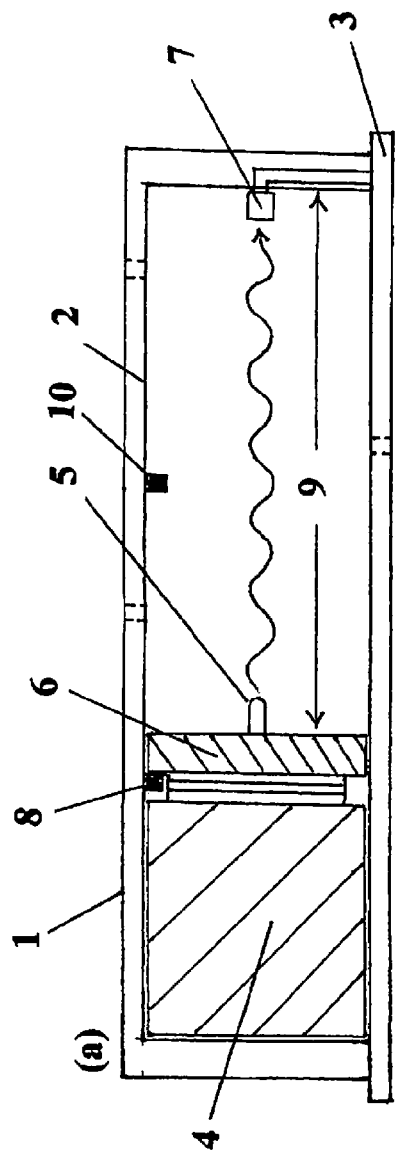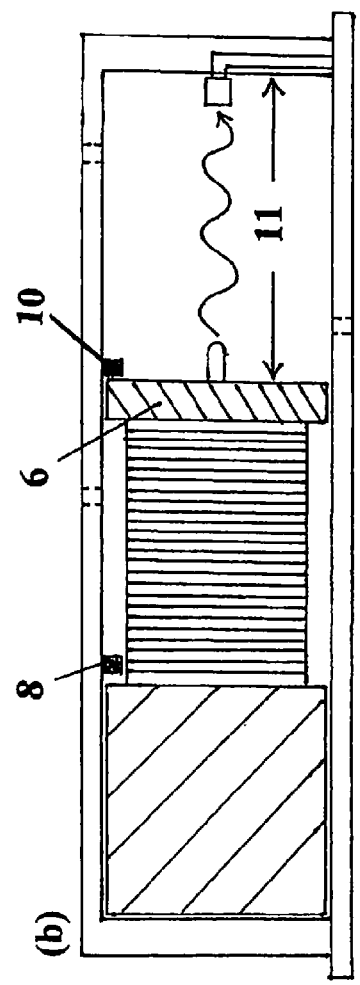
FIG. 1A
FIG. 1B

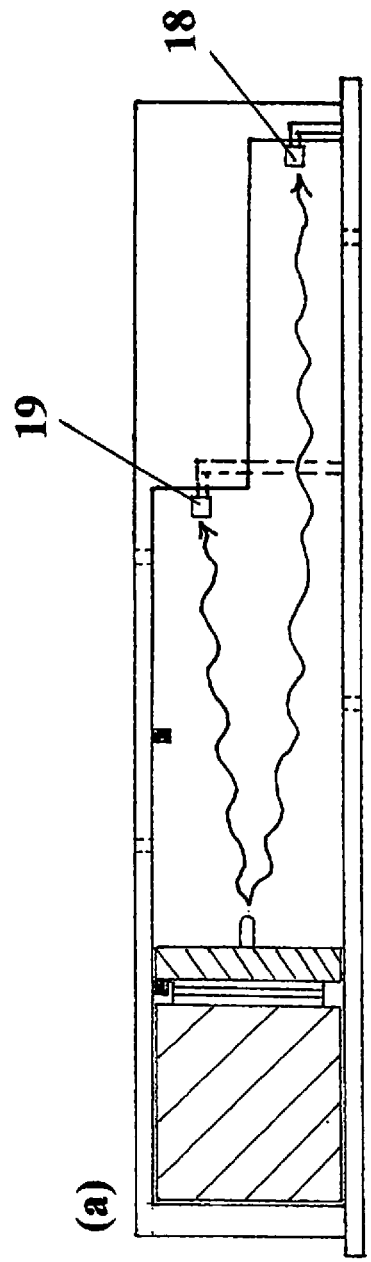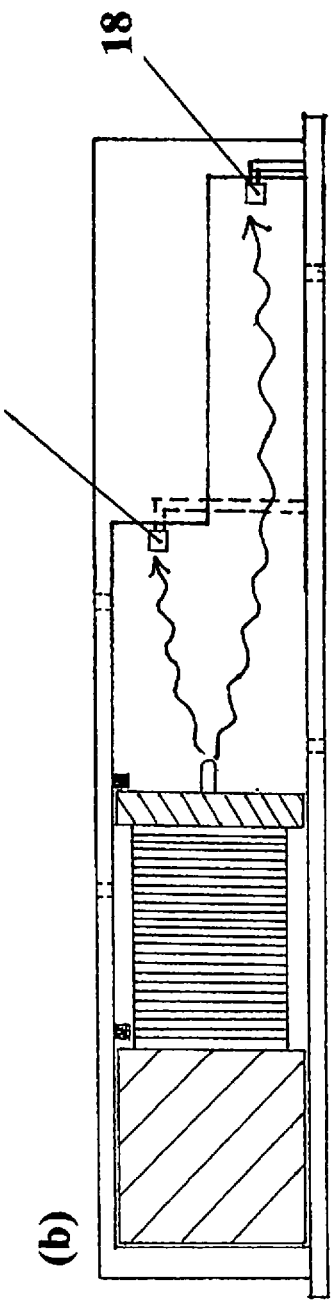
FIG. 4A
FIG. 4B

ABSORPTION BIASED SINGLE BEAM NDIR GAS SENSOR

CROSS-REFERENCE TO RELATED APPLICATIONS

This application is a non-provisional application of U.S. Patent Application No. 61/891,222, of the same title, filed on Oct. 15, 2013, the disclosure of which is specifically incorporated herein by reference.

FIELD OF THE INVENTION

The present application is in the field of gas analysis, and specifically relates to apparatus using a Non-Dispersive Infrared (NDIR) gas analysis technique to determine the concentration of a particular type of gas present in a chamber by sensing the absorption of infrared radiation passing through the gas.

BACKGROUND OF THE INVENTION

All molecules vibrate and rotate at characteristic frequencies in the electromagnetic spectrum. These vibration/rotational frequencies cause asymmetric molecules such as $CO_2$ and $H_2O$, but not symmetric molecules like $N_2$ or $O_2$, to absorb light at very specific wavelengths, particularly in the infrared. The NDIR gas measurement technique targets these characteristic absorption bands of asymmetric molecules of gases in the infrared for their detection. The term "non-dispersive" which actually implies "non-spatially-dispersive" as used herein refers to the apparatus used, typically a narrow-band infrared transmission filter instead of a spatially-dispersive element such as a prism or diffraction grating, for isolating for the purpose of measurement the radiation in a particular wavelength band that coincides with a strong absorption band of a gas to be measured.

The NDIR technique has long been considered as one of the best methods for gas measurement. In addition to being highly specific, NDIR gas sensors are also very sensitive, relatively stable and easy to operate and maintain. In contrast to NDIR gas sensors, the majority of other types of gas sensors today are in principle interactive. Interactive gas sensors are less reliable, short-lived and generally non-specific, and in some cases can be poisoned or saturated into a non-functional or irrecoverable state.

Despite the fact that interactive gas sensors are mostly unreliable and that the NDIR gas measurement technique is one of the best there is, NDIR gas sensors still have not enjoyed widespread high volume usage to date. The main reasons for this can generally be attributed to their high unit production cost, relatively large size and output drifts over time.

Just about all gas sensors ever designed and manufactured to date, irrespective of what technology is being employed, invariably have significant output drifts over time. While NDIR gas sensors can be recalibrated as part of a periodic maintenance program or service, the cost of such recalibration has prevented NDIR gas sensors from being widely adopted for many applications.

Recently the present author in U.S. Pat. No. 8,143,581, the disclosure of which is specifically incorporated by reference herein, advanced the teaching of an Absorption Biased ("AB") NDIR Gas Sensing Methodology which is capable of significantly reducing sensor output drifts over time. This AB methodology can be reviewed briefly as follows. First of all, this methodology is based upon a conventional Double Beam Configuration Design for NDIR gas sensors. Two channels or beams are set up, one labeled Signal and the other Reference. Both channels share a common infrared source but have different detectors, each of which is equipped with the same or identical narrow band-pass filter used to spectrally define and detect the target gas of interest. Both detectors for the two channels share the same thermal platform with each other and also with the sample chamber and the common infrared source mount for the sensor. An absorption bias is deliberately established between the Signal and Reference channels by having the sample chamber path length longer for the Signal channel than that for the Reference channel. By so doing, the detector output of the Reference channel is always greater than that of the Signal channel when there is target gas present in the sample chamber. This is due to the fact that there is more absorption taken place in the Signal channel because of its longer sample chamber path length. By applying this absorption bias between the Signal and Reference channels, one is able to calibrate the sensor even when both channel detectors have the same and identical narrow band-pass filters.

The Absorption Biased ("AB") NDIR gas sensing methodology addresses directly a serious technical weakness never recognized by engineers for decades in the design of the conventional and the most popular Double Beam Configuration NDIR gas sensors. In this conventional design, a Signal channel and a Reference channel are set up between the shared blackbody source and two infrared detectors. The Signal channel detector is equipped with a narrow band-pass filter which is used to spectrally define and detect the target gas of interest. The Reference channel detector is on the other hand equipped with a narrow band-pass filter which is located spectrally away from the absorption band of the target gas of interest and is also neutral to the absorption bands of all other common gases present in the atmosphere. According to the rationale for the design of the Double Beam methodology, the addition of a Reference channel operating at a different wavelength off the Signal channel absorption one and then processing the ratio of the signals of the two channels as the sensor output will eliminate or reduce many error-causing factors common to both channels. While the Double Beam design is no doubt superior to the Single Beam one, it has overlooked one major technical problem for this design which for decades has caused output drifts over time for NDIR gas sensors.

The problem referred to above has to do with the aging of the blackbody source common to both the Signal and the Reference channels. As the blackbody source ages, its operating temperature and therefore output will inevitably change, not only in magnitude (radiation intensity) but also in spectral content, as dictated by Planck's radiation law for blackbodies with different temperatures. Since the Signal channel filter and the Reference channel filter each passes radiation of a different wavelength from the blackbody source to their respective detectors, their signal ratio will change as the spectral content of the source changes causing the sensor output to inevitably drift over time. The Absorption Biased ("AB") methodology discussed earlier above addresses this problem head-on by applying the same spectral narrow band-pass filter for target gas detection to both the Signal and the Reference channels. An absorption bias is then applied to the Signal channel by making the sample chamber path length associated with it longer than that associated with the Reference channel. In this way even though both the Signal and the Reference channels have the same spectral filter, the sensor can still be calibrated for the amount of target gas present in the sample chamber because of the absorption bias applied.

The present invention advances a more reliable NDIR gas technique and sensor which will remain more stable over time, while also reducing unit production cost and size. The present invention does this by improving upon the AB methodology.

SUMMARY OF THE INVENTION

The present invention is generally directed to a modification of the design configuration of the Absorption Biased (AB) methodology for NDIR gas sensors which has the Signal channel and the Reference channel physically separated in space as disclosed in U.S. Pat. No. 8,143,581 (Mar. 27, 2013). Other than spectral changes of the source, which is taken care of by the previously disclosed AB methodology, if any of the components of the sensor belonging separately to the two channels age differently, they can also cause the sensor output to drift. The current invention advances a simpler design for the sensor components arrangement for the AB designed NDIR gas sensor having the Signal and the Reference channels sharing effectively the same physical space thus rendering it virtually into a Single Beam configuration.

By utilizing only a single infrared source and a single thermopile detector equipped with a narrow bandpass filter designed to detect the gas of interest, the Absorption Biased characteristic feature can be reproduced by positioning alternately in time the single infrared source or the single infrared detector into two distinct location arrangements X and Y with respect to each other. This means that the source and/or the detector are moved alternately in time into location arrangements X and Y. For example, location arrangement X can provide the sensor with a longer pathlength (distance between source and detector) than that provided by arrangement Y, thereby creating an absorption bias for the sensor. In the context of the AB designed NDIR gas sensor, location arrangement X for the source and detector represents the Signal channel (longer sample chamber pathlength) and location arrangement Y represents the Reference channel (shorter sample chamber pathlength). Like in the case of the AB designed NDIR gas sensor, the ratio of the output of the Signal channel, measured during location arrangement X, over that of the Reference channel, measured during location arrangement Y, will be used to process the gas measurement. The advantage of this design configuration is that since there is only one set of components for the sensor belonging to both the Signal channel and the Reference channel inclusive of the infrared source, the sample chamber and the thermopile detector with the gas specific filter, and the ratio of the Signal channel output over that of the Reference channel is used to process the gas measurement, any aging effects of the common sensor components will be cancelled out and the output of the sensor will remain drift free over time.

Accordingly, it is a primary object of the present invention to advance an NDIR gas sensor methodology which, when appropriately implemented to an NDIR gas sensor, will render its output substantially stable or drift free over time.

This and further objects and advantages of the present invention will be apparent to one of ordinary skill in the art in view of the drawings and the detailed description of the invention set forth below.

BRIEF DESCRIPTION OF THE DRAWING

FIGS. 1A and 1B depict the conceptual design configuration for the sensor components of the current invention with FIG. 1A showing a movable source in the X arrangement for the Signal channel and FIG. 1B showing the movable source in the Y arrangement for the Reference channel.

FIGS. 4A and 4B depict the conceptual design configuration for the current invention used as multi-component gas detector while accommodating the fact that one or more of the gases to be detected have weaker absorption bands than the others and therefore require a longer sample chamber path length.

DETAILED DESCRIPTION OF THE INVENTION

Figure 2:
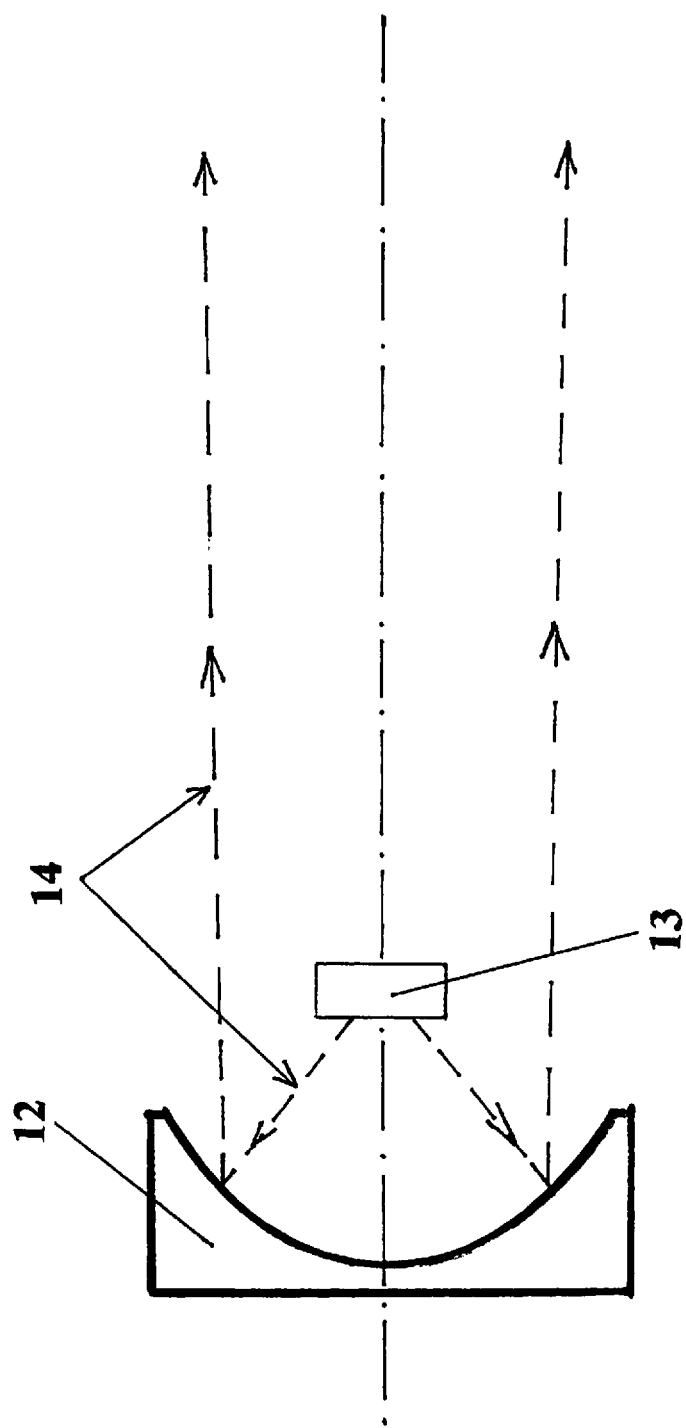
FIG. 2 depicts the conceptual arrangement for an infrared source transforming its radiation output substantially into a beam with the use of an optical device like a paraboloidal mirror.

The present invention uses the AB methodology to reduce NDIR gas sensor drift over time and further reduces such drift, as well as unit production cost and sensor size, by using a single infrared source and a single gas detector (for a chosen gas) which are moved in relationship to each other to create the Signal and Reference channels needed for the AB methodology.

FIGS. 1A and 1B depict a conceptual design configuration for the sensor components of a preferred embodiment of the present invention utilizing a Linear Voice Coil Motor (LVCM) as a motion device for temporally changing the configuration of the sample chamber between two distinct location arrangements. The sensor has a casing 1 within which is a sample chamber 2 anchored onto printed circuit board (PCB) 3 housing all the electronic processing circuitries of the sensor. Within sample chamber 2 resides a LVCM 4 with an infrared source 5 mounted at its movable end 6. Installed at the other end of sample chamber 2 is an infrared detector 7 facing directly opposite infrared source 5. When movable end 6 of LVCM 4 is restrained motionless by stop 8 going in a direction from right to left in a position called arrangement X as shown in FIG. 1A, the sensor assumes a Signal channel configuration having a sample chamber path length 9. When movable end 6 of LVCM 4 is restrained motionless by stop 10 going in a direction from left to right in a position called arrangement Y as shown in FIG. 1B, the sensor assumes a Reference channel configuration having a sample chamber path length 11 which is shorter than sample chamber path length 9 belonging to the Signal channel.

When LVCM 4 drives its movable end 6 carrying infrared source 5 alternately from location arrangement X [see FIG. 1A] to location arrangement Y [see FIG. 1B], the sensor will assume, respectively, a Signal channel configuration and a Reference channel configuration. By taking the ratio of the detector output for the Signal channel over that for the Reference channel in successive time sequence as a way to process the sensor signal for gas measurement, this is equivalent to the Absorption Biased methodology except for the fact that the Signal and the Reference channels are no longer separated physically in space. Furthermore, if the output radiation pattern of source 5 [see FIGS. 1A and 1B] is transformed into one that simulates a beam via the use of an optical focusing element like a paraboloidal mirror (see FIG. 2), the aging effect of the reflecting walls of the sample chamber will be rendered immaterial. As shown in FIG. 2, paraboloidal mirror 12 focuses the radiation of infrared source 13 approximately into a radiation beam of finite angular extent 14 so that this beam is never reflected by the walls of the sample chamber before reaching infrared detector 7 [see FIGS. 1A and 1B].

Figure 3:
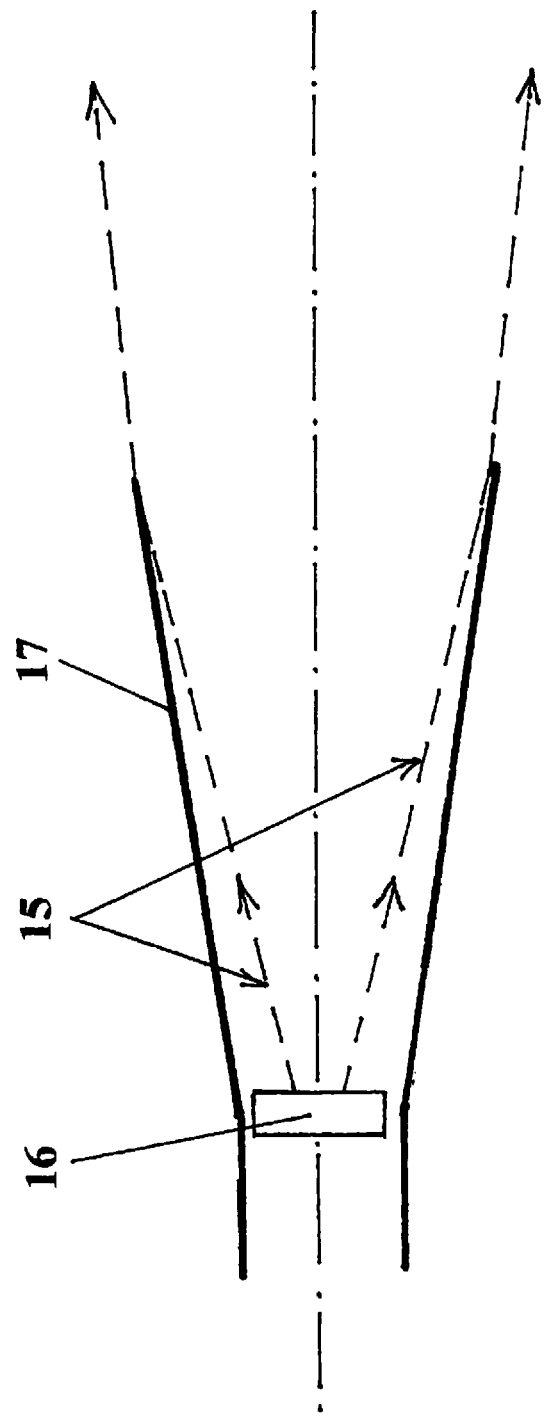
FIG. 3 depicts the conceptual arrangement for an infrared source limiting its angular radiation output extent with the use of a collimating aperture device.

Or, if the emission angle of the radiation pattern from source 5 [see FIGS. 1A and 1B] is limited to 45° or less with the use of a collimating aperture (see FIG. 3), the aging effect of the reflecting walls of the sample chamber can also be reduced significantly. As shown in FIG. 3, the angular extent of output radiation 15 from source 16 is limited by collimating aperture device 17 to less than 45°. With this consideration in mind, all the critical components of the sensor disclosed in the current invention, inclusive of the source, sample chamber, band-pass filter and detector, are common between the Signal and Reference channels. Because the sensor now has only one source and one detector, it might be classified as a Single Beam NDIR gas sensor when classified from the standpoint of its physical elements although it might also be classified as a Double Beam (or dual channel) NDIR gas sensor when classified from the standpoint of its signal processing. It is this unique combination of physical elements and signal processing which is central to the present invention.

An advantage of the current invention is that because there is only one set of common sensor components which belongs to both the Signal and the Reference channels, any aging effects of these common components will be completely cancelled out by the ratio processing technique of the Absorption Biased NDIR gas sensing methodology. One additional advantage of the current invention over the Absorption Biased methodology is that the ambient temperature correction for the performance characteristics of the sensor components will no longer be needed since they are common to both to Signal and the Reference channels and therefore cancelled out. However, it is well known that the measurement of gas concentration using the NDIR technique depends on the gas density inside the sample chamber, thus the ambient temperature of the gas sample must still be accounted for with respect to the sensor calibration temperature according to the Ideal Gas Law of PV=nRT.

The current invention is not limited only to moving the infrared source as a way to achieve an Absorption Biased Single Beam NDIR gas sensor. In an equivalent way one can also move the detector as a way to achieve the same result, or even move both the infrared source and the detector, although such an embodiment is not as preferred. Furthermore, should the detector be replaced by a multichannel one, the current invention will become an Absorption Biased Multichannel Single Beam NDIR gas sensor assuming that the common sample chamber path length is adequate for use in the detection of multiple gases. For the case when the absorption strength of one or more of the multiple gases to be detected is weaker than the others and therefore requires a longer sample chamber path length, a configuration of sensor components such as that shown in FIGS. 4A and 4B can be applied. As shown in FIGS. 4A and 4B, the detectors employed to detect the concentration level for the weaker gases 18 are physically placed behind those detectors 19 for detecting the other gases. Such a sensor components configuration as shown in FIGS. 4A and 4B is consistent with the embodiment concept of the present invention.

The current invention is not limited only to moving either the infrared source and/or the detector by use of a Linear Voice Coil Motor (LVCM), but is also contemplated to cover any motion device that allows the temporal creation of both a signal path length and reference path length while still using a single source and a single detector to detect a single gas of interest. Some examples of other motion device that can accomplish the same purpose include, but are not limited to, motion devices that use an electromagnet, a permanent magnet, a spring or a combination thereof with at least one motion stop.

While the invention has been described herein with reference to a preferred embodiment, this embodiment has been presented by way of examples only, and not to limit the scope of the invention. Additional embodiments thereof will be obvious to those skilled in the art having the benefit of this detailed description. For example, there may be many different ways of moving either the infrared source and/or the detector for creating a different signal channel path length from the reference channel path length. Further modifications are also possible in alternative embodiments without departing from the inventive concept.

Accordingly, it will be apparent to those skilled in the art that still further changes and modifications in the actual concepts described herein can readily be made without departing from the spirit and scope of the disclosed inventions.

What is claimed is:

1. A Non-Dispersive Infrared ("NDIR") gas sensor for detecting the presence of a chosen gas, comprising:
    a single infrared source for generating infrared radiation into a sample chamber to illuminate a signal channel path length and a reference channel path length, the signal channel path length being longer than the reference channel path length, the reference channel path length being a non-zero length;
    a detector with a specific spectral filter for detecting the chosen gas;
    a motion device that alternates the distance between the single source and the detector representing respectively the signal channel path length and the reference channel path length; and
    electronics for determining a sample concentration of the chosen gas by use of an absorption biased methodology;
    wherein the absorption bias methodology uses a ratio of a signal channel output ("$V_S$") obtained by the detector at a first point of time when the distance between the single infrared source and the detector is the signal channel path length over a reference channel output ("$V_R$") obtained by the detector at a second point of time when the distance between the single infrared source and the detector is the reference channel path length;
    wherein the ratio is based upon a successive time sequence between the first and the second points of time that approximates a simultaneous time sequence for purposes of the absorption bias methodology.

2. The NDIR gas sensor of claim 1, wherein the motion device moves the single infrared source between a first position for the signal channel path length and a second position for the reference channel path length.

3. The NDIR gas sensor of claim 1, wherein the motion device is a Linear Voice Coil Motor (LVCM).

4. The NDIR gas sensor of claim 1, wherein both $V_S$ and $V_R$ are obtained by use of an identical set of optical components.

5. The NDIR gas sensor of claim 1, wherein the signal channel path length contains an additional length of the sample chamber that is not contained in the reference channel path length.

6. The NDIR gas sensor of claim 1, wherein the motion device moves the infrared source to expose the additional length of the sample chamber.

7. The NDIR gas sensor of claim 6, further comprising:
    a beam pattern control for limiting an initial beam radiation pattern for the single infrared source.

8. The NDIR gas sensor of claim 7, wherein the beam pattern control is comprised of an optical collimating device.

9. The NDIR gas sensor of claim 1, wherein the detector is a multichannel detector with a plurality of spectral filters for detecting a plurality of chosen gasses.

10. The NDIR gas sensor 9, wherein the electronics determines the sample concentration of the plurality of chosen gases by use of the absorption bias methodology.

11. The NDIR gas sensor of claim 1, further comprising:
at least one additional detector with at least one additional spectral filter for detecting at least one additional chosen gas; and
electronics for determining the sample concentration of the at least one additional chosen gas by use of the absorption bias methodology.

12. A Non-Dispersive Infrared ("NDIR") gas sensor for detecting the presence of a plurality of chosen gases, comprising:
a single infrared source for generating infrared radiation into a sample chamber to illuminate a signal channel path length and a reference channel path length, the signal channel path length being longer than the reference channel path length, the reference channel path length being a non-zero length;
a detector with a plurality of spectral filters for detecting the plurality of chosen gases;
a motion device that moves the single infrared source between a first position for the signal channel path length and a second position for the reference channel path length; and
electronics for determining a sample concentration of each of the plurality of chosen gases by use of an absorption bias methodology;
wherein the detector is a multichannel detector for detecting the presence of the plurality of chosen gases; and
wherein the absorption bias methodology uses a ratio of a signal channel output ("$V_S$") obtained by the detector at a first point of time when the distance between the single infrared source and the detector is the signal channel path length over a reference channel output ("$V_R$") obtained by the detector at a second point of time when the distance between the single infrared source and the detector is the reference channel path length;
wherein the ratio is based upon a successive time sequence between the first and the second points of time that approximates a simultaneous time sequence for purposes of the absorption bias methodology.

13. The NDIR gas sensor of claim 12, wherein both $V_S$ and $V_R$ are obtained by use of an identical set of optical components.

14. The NDIR gas sensor of claim 12, wherein the plurality of chosen gases is comprised of carbon monoxide and carbon dioxide.

15. The NDIR gas sensor of claim 12, further comprising:
at least one additional detector with at least one additional spectral filter for detecting at least one additional chosen gas; and
electronics for determining the sample concentration of the at least one additional chosen gas by use of the absorption bias methodology.

16. A Non-Dispersive Infrared ("NDIR") gas sensor for detecting the presence of a plurality of chosen gases, comprising:
a single infrared source for generating infrared radiation into a sample chamber;
a first detector with a first spectral filter for detecting a first chosen gas in the sample chamber;
a second detector with a second spectral filter for detecting a second chosen gas in the sample chamber, said second detector being located more distant from the single infrared source than the first detector;
a motion device that moves the single infrared source between a first position for the signal channel path length and a second position for the reference channel path length, the reference channel path length being a non-zero length; and
electronics for determining a sample concentration of each of the plurality of chosen gases by use of an absorption bias methodology;
wherein the absorption bias methodology uses a ratio of a signal channel output ("$V_S$") obtained by each detector at a first point of time when the distance between the single infrared source and each detector is the signal channel path length over a reference channel output ("$V_R$") obtained by each detector at a second point of time when the distance between the single infrared source and each detector is the reference channel path length;
wherein the ratio is based upon a successive time sequence between the first and the second points of time that approximates a simultaneous time sequence for purposes of the absorption bias methodology.

17. The NDIR gas sensor of claim 16, wherein at least one of the first and the second detectors is a multichannel detector with a third spectral filter that is used to detect a third chosen gas.

18. The NDIR gas sensor of claim 16, wherein both of the first and the second detectors are a multichannel detector with a plurality of spectral filters that is used to detect at least two of the plurality of chosen gases.

* * * * *